(12) United States Patent
von Herrath (10) Patent No.: US 6,884,785 B2
(45) Date of Patent: Apr. 26, 2005

(54) COMPOSITIONS AND METHODS FOR THE TREATMENT OR PREVENTION OF AUTOIMMUNE DIABETES

(75) Inventor: Matthias G. von Herrath, Del Mar, CA (US)

(73) Assignee: The Scripps Research Institute, La Jolla, CA (US)

( * ) Notice: Subject to any disclaimer, the term of this patent is extended or adjusted under 35 U.S.C. 154(b) by 52 days.

(21) Appl. No.: 09/336,672

(22) Filed: Jun. 17, 1999

(65) Prior Publication Data

US 2002/0107210 A1 Aug. 8, 2002

(51) Int. Cl.$^7$ .................. A61K 31/711; C07H 21/04; C12N 15/85

(52) U.S. Cl. .................. 514/44; 536/23.1; 536/23.5; 536/24.1; 424/184.1; 424/185.1; 424/198.1; 424/278.1; 435/320.1

(58) Field of Search .................. 514/44; 536/23.1, 536/23.5, 24.1; 435/320.1, 7.1; 424/184.1, 185.1, 198.1, 278.1

(56) References Cited

U.S. PATENT DOCUMENTS

| | | | | |
|---|---|---|---|---|
| 5,891,435 A | * | 4/1999 | Muir et al. | 424/185.1 |
| 5,951,976 A | * | 9/1999 | Segal | 424/93.21 |
| 6,207,159 B1 | * | 3/2001 | Kaufman et al. | 424/184.1 |
| 6,313,272 B1 | * | 11/2001 | Greve et al. | 530/351 |

FOREIGN PATENT DOCUMENTS

| | | | | |
|---|---|---|---|---|
| WO | WO 95/06718 | * | 3/1995 | 435/325 |
| WO | WO 95/21926 | * | 8/1995 | 435/6 |
| WO | WO 9745144 A | | 4/1997 | |
| WO | WO 97/46253 | * | 12/1997 | 424/184.1 |
| WO | WO 98/24908 | * | 6/1998 | 435/455 |
| WO | WO 0020457 A | | 4/2000 | |

OTHER PUBLICATIONS

Tokui et al. Suppressive effect on the development of insulin–dependent diabetes mellitus in nonobese diabetic mice by intramuscular injection of plasmid DNA expressing glutamic acid decarboxylase (GAD) adn interleukin–4 (IL–4). Bunshi Tonyobyogaku Vo.*

Ally et al. Prevention of autoimmune disease by retroviral-mediated gene therapy. J. Immunol. vol. 155:5404–5408, Nov. 1995.*

Prud'homme et al. Prevention of autoimmune diabetes by intramuscular gene therapy with a nonviral vector encoding an interferon–gamma receptor/lgG1 protein. Gene Therapy vol. 6:771–777, May 1999.*

Giannoukakis et al. Perspectives in Diabetes: Targeting autoimmune diabetes with gene therapy. Diabetes vol. 48:2107–2121, Nov. 1999.*

Liu et al. Intramuscular injectionof plasmid DNA encoding intracellular or secreted glutamic acid decarboxylase causes decreased insulitis in the non–obese diabetic mouse. Gene Therapy and Molecular Biology. vol. 3:197–206, Dec. 1998.*

Von Herrath, M.G. et al.: "In vivo treatment with a MHC class I–restricted blocking peptide can prevent virus–induced autoimmune diabetes" Journal of Immunology, vol. 161, No. 9, Nov. 1, 1998, pp. 5087–5096, XP0000919064 the whole document.

Coon et al., "DNA immunization to prevent autoimmune diabetes" J,. Clin. Invest., 104/2:189–194, 1999.

von Herrath et al., "Role of viruses in type I diabetes", Seminars in Immunology, 10:87–100, 1998.

von Herrath et al., "How Virus Induces a Rapid or Slow Onset Insulin–Dependent Diabetes Mellitus in a Transgenic Model", Immunity, 1:231–242, 1994.

von Herrath et al., "Coexpression of B7–1 and Viral ("Self") Transgenes in Pancreatic β Cells Can Break Peripheral Ignorance and Lead to Spontaneous Autoimmune Diabetes", Immunity, 3:727–738, 1995.

von Herrath et al., "Oral Insulin Treatment Suppresses Virus–induced Antigen–specific Destruction of β Cells and Prevents Autoimmune Diabetes in Transgenic Mice", J,. Clin. Invest., 98/6:1324–1331, 1996.

von Herrath and Oldstone, "Interferon–γ Is Essential for Destruction of β Cells and Development of Insulin–dependent Diabetes Mellitus", J,.Exp. Med., 185/3:531–539, 1997.

von Herrath and Oldstone, "Virus–induced autoimmune disease", Current Opinion in Immunology, 8/878–885, 1996.

von Herrath and Oldstone, "Pathological Changes in the Islet Milieu Precede Infiltration of Islets and Destruction of β Cells by Autoreactive Lymphocytes in a Transgenic Model of Virus–Induced IDDM", J,.Autoimmunity, 10:231–239, 1997.

Holz et al., "Disruption of the STAT4 Signaling Pathway Protects from Autoimmune Diabetes While Retaining Antiviral Immune Competence",J. Immunology, pp. 5374–5382, 1999.

Homann et al., "Autoreactive DC4 $^+$ T Cells Protect from Autoimmune Diabetes via Bystander Suppression Using the IL–4/Stat6 Pathway", Immunity, 11:463–472, 1999.

Liu et al., "Intramuscular injection of plasmid DNA encoding intracellular or secreted gultamic acid decarboxylase causes decreased insulitis in the non–obese diabetic mouse," Gene Ther Mol Biol. 3:197–296, 1998.

* cited by examiner

Primary Examiner—David Guzo
(74) Attorney, Agent, or Firm—DLA Piper Rudnick Gray Cary US LLP (57) ABSTRACT

The present invention provides compostions and methods for the prevention or treatment of autoimmune disorders. In particular, the invention methods utilize genetic material encoding at least a portion of an autoreactive epitope that, upon administration to a subject, acts to modulate the immune system thereby ameliorating conditions associated with an autoreactive antigen.

8 Claims, 3 Drawing Sheets

FIG. 1

Immunization with DNA plasmids expressing the insulin B chain, but not the LCMV NP, is effective in preventing IDDM in RIP-NP mice

FIG. 2

SEQUENCE LISTING

```
<160> NUMBER OF SEQ ID NOS: 1

<210> SEQ ID NO 1
<211> LENGTH: 9
<212> TYPE: PRT
<213> ORGANISM: Lymphocytic chiromeningitis virus

<400> SEQUENCE: 1

Arg Pro Gln Ala Ser Gly Val Tyr Met
1               5
```

COMPOSITIONS AND METHODS FOR THE TREATMENT OR PREVENTION OF AUTOIMMUNE DIABETES

ACKNOWLEDGEMENT OF GOVERNMENT SUPPORT

This invention was made with government support under Contract Nos. AI44451 and DK51091 by the National Institutes of Health. The government has certain rights in the invention.

FIELD OF THE INVENTION

The present invention relates generally to regulation of the immune system, and more specifically to compositions and methods for the prevention or treatment of autoimmune disorders. In particular, the invention methods utilize genetic material encoding at least a portion of an autoreactive antigen or epitope that, upon administration to a subject, acts to modulate the immune system thereby ameliorating conditions associated with such an autoantigen or other autoantigens.

BACKGROUND OF THE INVENTION

Vertebrates possess the ability to mount an immune response as a defense against pathogens from the environment as well as against aberrant cells, such as tumor cells, which develop internally. This can take the form of innate immunity, which is mediated by NK cells, neutrophils and cells of the monocyte/macrophage lineage, or the form of acquired or active immunity against specific antigens mediated by lymphocytes. Active immune responses can be further subdivided into two arms, the humoral response which entails the production of specific antibodies that serve to neutralize antigens exposed to the systemic circulation and aid in their uptake by professional phagocytic cells, and the cellular arm which is required for recognition of infected or aberrant cells within the body.

In both cases the specific response is regulated by the intracellular processing and recognition of the antigen by effector T-cells. Mature cytolytic T lymphocytes (CTLs) or T helper cells (Th) in general remain in a resting state unless they encounter antigens that their receptors can recognize in the context of MHC class I or II molecules. Upon encountering the specific antigens, the T-cells proliferate and perform effector functions, the result of which is elimination of the reactive antigens. When the antigen is processed through the cytoplasmic route, the resulting peptides are bound to nascent MHC class I molecules which facilitate appropriate presentation to effector T-cells. MHC class I presentation favors recognition by cytotoxic T lymphocytes (CTLs) that carry the CD8 ligand. In contrast, intracellular processing via the endocytic route results in presentation on MHC class II molecules which favors T helper responses involved in stimulation of both, humoral and cellular arms. The goal of vaccination is to prime both responses and generate memory T cells, such that the immune system is primed to react to a pathogenic infection. Engagement of both the humoral and cellular immune responses leads to broad based immunity and is the preferred goal for intracellular pathogens.

Activation of the T cells entails the generation of a series of chemical signals (primarily cytokines) that result in direct action or stimulation of other cells of the immune system to act. In the case of activation by class I MHC-antigen, CTLs proliferate and act to destroy infected cells presenting that given antigen in form of an MHC bound peptide. Killing an infected cell prevents the virus from proliferating and makes it accessible to neutralizing antibodies, and hence permitting elimination of the virus. In contrast, activation of Th cells by class II MHC-antigen complexes does not destroy the antigen presenting cell (which is part of the host's defense system) but rather stimulates the Th cell to proliferate and generate signals (again primarily cytokines) that affect various cells. Among other consequences, the signaling leads to B cell stimulation, macrophage activation, CTL differentiation and promotion of inflammation. This concerted response is relatively specific and is usually directed to foreign elements bearing the peptide presented by the class II MHC system.

When operating properly, the immune response is surprisingly effective at eliminating microscopic pathogens and, to a lesser extent, neoplastic cells. In general, the complicated mechanisms for self-recognition are efficient and allow a strong response to be directed exclusively at eliminating foreign antigens. The regulation of self/non-self discrimination, which is a critical function of the immune system, involves multiple mechanisms during the development and life-span of T and B lymphocytes. Whereas deletion of self-reactive T and B cell precursors in the central lymphoid organs eliminates most of the autoreactive cells, the peripheral mechanisms that require Fas, IL-2R and CTLA-4 mediated signaling are thought to be crucial for the immune homeostasis. Unfortunately, the immune system occasionally malfunctions and turns against the cells of the host thereby provoking an autoimmune response. Autoimmunity or autoreactivity typically occurs when antigen receptors on immune cells recognize specific self-antigens (e.g. self-epitopes) on host cells and initiate reactions that result in the destruction of the host cells. In many cases, autoimmune reactions are self-limited in that they disappear when the antigens that provoked them are cleared away. However, in some instances the autoreactive lymphocytes survive longer than they should and continue to induce apoptosis or otherwise eliminate host cells. Some evidence in animals and humans indicates that extended survival of autoreactive cells is implicated in at least two chronic autoimmune disorders, systemic lupus erythematosus and rheumatoid arthritis.

Other mechanisms of action are also thought to contribute to the development of various autoimmune disorders. For example, over the last few years it has become clear that the avidity of T cell-APC interactions dictates thymic learning and tolerance to self antigens. Accordingly, high avidity interactions lead to elimination of the T cell whereas low avidity interactions allow for maturation and exit from the thymus. Although this mechanism is effective in purging the immune system of autoreactivity, T cell precursors endowed with self reactivity could still be generated and migrate to the periphery if the autoantigen is sequestered and does not achieve effective levels of thymic presentation, is subjected to thymic crypticity or is poorly presented. Moreover, superantigens capable of reacting with particular T cell receptors and events that could stimulate antigen mimicry, epitope spreading or peripheral loosening in peptide crypticity may trigger activation of those self-reactive T cells and cause antigen exposure. In any case, continuous supply of autoantigen and abundant generation of T cell receptor ligands (peptide-MHC complexes) are a likely mechanism of T cell aggressiveness. Examples of conditions resulting from a spontaneous break in self-tolerance include multiple sclerosis (MS), rheumatoid arthritis (possibly more than one mechanism), lupus erythrematosis and type I diabetes all of which are thought to be T cell mediated autoimmune diseases (myaestenia gravis-break from self tolerance but Ab driven, inflammatory bowel disease (Chrohn's)).

One of the most likely scenarios regarding the pathogenesis of an autoimmune disease like type I diabetes, may begin with abnormal regulation of autoreactive T cells either due to bystander activation or due to molecular mimicry. For example, a viral infection or exposure to a superantigen may provide sufficient co-stimulation resulting in activation of few low affinity autoreactive T cells that escape the thymus selection. Abnormal down-regulation of such autoreactive responses may lead to expansion of pathogenic T cells that infiltrate the organ where the recognized antigen is present. A few host-related factors facilitate the transition between non-pathogenic autoreactivity and autoimmune disease: leaky central negative selection allowing the escape of higher numbers of autoreactive precursors; impaired peripheral tolerance due to abnormalities involving receptors or ligands that mediated down-regulation of lymphocyte activity; a bias to generate Th1 pro-inflammatory responses as opposed to more balanced Th1/Th2 responses; high frequency and abnormal activity of professional APCs. Local inflammation and direct destruction of host cells trigger antigen release, uptake by professional APCs and presentation to specific T cells, thus perpetuating a positive feedback that exacerbates the autoimmunity. Simultaneously, normally cryptic, organ-associated antigens may become exposed in the context of activation of professional antigen presenting cells and antigen release, resulting in activation of T cells specific for these other self antigens. Particularly in conditions favoring overall Th1/Th2 imbalance, the employment of additional specificities may accelerate the disease. It is widely believed that whereas Th1 cytokines like IFN-γ contribute to the pathogenesis of autoimmunity, Th2 cytokines like IL-4 and IL-10 may suppress the activity of pathogenic Th1 or Tc1 cells.

Regardless of which mechanism is responsible for the malfunction of the immune system in autoimmune diseases, the results can be devastating to the individual. For example, multiple sclerosis is a chronic, inflammatory disorder that affects approximately 250,000 individuals in the United States. The inflammatory process occurs primarily within the white matter of the central nervous system and is mediated by activated T cells, B cells and macrophages which are responsible for the demyelination of the axons. Although the clinical course can be quite variable, the most common form is manifested by relapsing neurological deficits including paralysis, sensory deficits and visual problems.

In another debilitating autoimmune disease, insulin-dependent diabetes mellitus (IDDM, type I diabetes or juvenile diabetes), the immune system attacks the insulin-producing beta cells in the pancreas and destroys them. A person with IDDM produces little or no natural insulin and requires daily injections of the hormone to stay alive. Each year, from 11,000 to 12,000 children are diagnosed with IDDM and, among the more than 7 million people in the United States who are being treated for diabetes, about 5 to 10 percent have IDDM. In young people, acute complications due to inadequately controlled glucose fluctuations pose the greatest threat to survival for people with IDDM. As people grow older, long-term complications resulting from damage to organs due to blood vessel deterioration become more important, resulting in, for example, peripheral neuropathy, nephropathy, and retinal degeneration.

Treatments for autoimmune diseases have reached limited success. For example, it is often possible to correct organ-specific autoimmune disease through metabolic control. Where function is lost and cannot be restored, mechanical substitutes or tissue grafts may be appropriate. However, although it may be possible to alleviate some of the symptoms no effective long-term curative treatment exists for several of the most disabling autoimmune disorders, including multiple sclerosis and IDDM. While a number of compounds, including insulin, corticosteroids and modified beta interferon, can ameliorate some of the symptoms of autoimmune diseases, they have proven to have serious side effects and/or require long term use.

Other avenues of treatment have shown promise in pre-clinical animal model studies but have yet to be shown to be effective in humans. One such therapy is the suppression of pathogenic lymphocytes by treatment with specific antigens. Such treatment may have the critical advantage of addressing only the specific T cells, while sparing the rest of the immune system. The exposure of autoreactive lymphocytes to increased doses of self-antigens may result in deletion or anergy which, in turn, can lead to prevention or suppression of the disease. Whereas this scenario may occur in certain circumstances, there are at least two factors that need to be considered: first, autoimmune diseases are likely to be associated with impaired peripheral regulatory mechanisms and secondly, once the disease becomes manifest, it may be associated with reactivity against multiple other self-antigens.

In view of these limitations, a more attractive strategy would be the generation of autoreactive cells with the ability to recognize organ specific antigens and to produce mediators that suppress the activity of pathogenic cells instead of having the potential to promote disease. For example, it would be desirable to selectively stimulate the production of immunomodulator compounds such as, for example, cytokines like IL-4, IL-10, IL-9, IL-13 and TGF-beta. It will be appreciated that the induction of such immunomodulator compounds may be associated with the identity of the selected epitope in the context of the T cell repertoire, the cytokine context during priming and the inoculation regimen/antigen timing and duration of inoculations. Significantly, it will be appreciated that such a strategy is not limited to antigens that are central to the pathogenesis of an autoimmune disease, but potentially employs any organ-specific antigen. As such, selective induction of such immunomodulator compounds has several advantages in the amelioration of autoimmune disorders. For example, such a treatment does not require identification of the those epitopes that trigger the pathogenesis rather it may offer broad-based bystander suppression of autoreactive harmful T cells against various epitopes. Moreover such a strategy would limit the risk of exacerbating the disease due to transient activation phase of pathogenic T cells during antigen therapy and it may circumvent the refractoriness of pathogenic T cells to peripheral tolerance mechanisms mediating anergy and deletion. Unfortunately, no method presently exists for selectively inducing immunomodulator compounds to reduce or prevent the symptoms associated with autoimmune disorders.

SUMMARY OF THE INVENTION

It will be appreciated that the invention may be used to treat any immune disorder that responds to the presentation of self-epitopes. This is particularly true of T cell mediated autoimmune disorders including, for example, multiple sclerosis, lupus, rheumatoid arthritis, scleroderma, insulin-dependent diabetes, myastenia gravis and ulcerative colitis. In a like manner, the present invention can be used to selectively down-regulate the immune system with respect to continuously presented agonists such as allergens. Further, the compounds and associated compositions of the present invention may be used to selectively suppress various components of the immune system to reduce the likelihood of tissue or organ rejection following transplant.

In addition to the aforementioned advantages, the compounds, compositions, and methods of the present invention may be used to induce tolerance to various autoantigens in neonates and infants. More particularly, the present invention further provides compositions and methods for conferring resistance in neonate or infant mammals to the induction of an autoimmune disease during adult life. In accordance with the teachings herein, this neonatal tolerance is characterized by a lymph node deviation and unusual gamma interferon-mediated splenic anergy upon challenge with the appropriate autoantigen. As discussed above, preferred embodiments the present invention may provide for the induction of the desired neonatal tolerance upon administration in a non-reactive carrier (i.e. those without adjuvants).

Accordingly, it is a general object of the present invention to provide methods and compositions for effectively modifying the immune system of a vertebrate for prophylactic and therapeutic purposes to treat or prevent an autoimmune disorder.

It is another object of the present invention to provide methods and compositions for the effective induction of regulatory cytokines to down-regulate the immune system of a mammal having an autoimmune condition.

It is yet another object of the present invention to provide methods and compositions for the treatment or prevention of insulin dependent diabetes.

In one aspect, the invention provides an immunomodulating composition for use in treating or preventing an autoimmune disorder comprising a nucleic acid construct encoding at least one epitope from a self-antigen in a pharmaceutically acceptable carrier. An exemplary epitope illustrated in the present invention is in insulin B chain.

In another aspect, the invention provides a method for treating or preventing autoimmune disorder in a subject having or at risk of having the disorder comprising administering to the subject, an immunomodulatory effective amount of a nucleic acid construct encoding at least one epitope from a self-antigen in a pharmaceutically acceptable carrier, wherein expression of the epitope provides a regulatory immune response, thereby treating or preventing the disorder. For example, the method provides an insulin B chain epitope for use in a subject having or at risk of having IDDM.

In a further aspect, the invention provides a method for inducing a regulatory immune response in a subject having or at risk of having an autoimmune disorder comprising administering to the subject, an immunomodulatory effective amount of a nucleic acid construct encoding at least one epitope from a self-antigen in a pharmaceutically acceptable carrier, wherein expression of the epitope provides a regulatory immune response.

It is envisioned that the compositions and methods of the invention include co-administration of the nucleic acid construct encoding at least one epitope from a self-antigen with a nucleic acid construct encoding a biological response modifier (e.g., a cytokine, chemokine, interferon, interleukin) or administering the nucleic acid construct encoding the at least one epitope from a self-antigen and also encoding at least one biological response modifier (e.g., IL-4).

Other objects, features and advantages of the present invention will be apparent to those skilled in the art from a consideration of the following detailed description of preferred exemplary embodiments thereof taken in conjunction with the figures which will first be described briefly.

BRIEF DESCRIPTION OF THE DRAWINGS

FIG. 1 illustrates immunization protocols used in the Examples set forth in the instant application. More specifically, genetic constructs according to the instant invention were given intramuscularly into the quadriceps femoris muscle on each side (2×50 micro-g in 50 micro-l saline) per injection, by one of the three illustrated protocols. Asterisks denote times at which LCMV (lymphocytic choriomeningitis virus-specific CTL responses were evaluated. The development of IDDM was followed for longer than 3 months post-LCMV infection.

FIG. 2 demonstrates that compositions of the instant invention may be employed to prevent the onset of diabetes in a murine model. RIP-NP transgenic mice were treated with pCMV-NP with pCMV-ins-B according to the protocols set forth in FIG. 1 or were fed oral porcine insulin as described herein. Diabetes (i.e. blood glucose consistently >350 mg/dl) was measured weekly for a total observation period of 3 months. Group sizes were as follows: 10 mice pCMV-B, 10 mice pCMV-NP, 10 mice oral porcine insulin with 10 untreated controls.

DETAILED DESCRIPTION OF THE INVENTION

The present invention is based on the seminal discovery that DNA immunization with plasmids expressing self-antigens provides a prophylactic and therapeutic approach to prevent autoimmune diseases. The inventors have shown that mice expressing lymphocytic choriomeningitis virus (LCMV) nucleoprotein (NP) as a transgene in their beta-cells develop IDDM only following LCMV infection. Inoculation of plasmid DNA encoding the insulin B-chain reduced the incidence of virally induced autoimmune diabetes (IDDM) by 50% in this model. The insulin B chain DNA vaccination was effective through induction of regulatory CD4 lymphocytes that react with the insulin B-chain, secrete IL-4 and locally reduce activity of LCMV-NP autoreactive CTL in the pancreatic draining lymph node. In contrast, similar vaccination with plasmids expressing the LCMV viral (self) protein did not prevent IDDM, because no such regulatory cells were induced.

In an exemplary model, the present invention shows that DNA vaccination with a plasmid expressing the insulin B-chain can effectively reduce autoimmune diabetes when given during the pre-diabetic phase. The protection is mediated by insulin-B reactive, IL-4 producing (TH2) lymphocytes, most probably of the CD4+ lineage, and does not result from a generalized/systemic reduction in the diabetogenic NP-specific effector cells, the activity and number of which remain unchanged. Rather protection results from "bystander suppression", induced in the islets or pancreatic draining node by the insulin B-specific CD4+ T cells, which leads to a significant local reduction in NP-specific autoreactive T-cells, potentially due to a lack of antigenic stimulation by antigen presenting cells exposed to IL-4.

Efforts to identify sequence homologies between self peptide epitopes that might be involved in autoimmunity and various bacterial and viral pathogens have therefore been made. These homology searches have focused on alignments with sequence identity. No success has been reported using such alignments in identifying epitopes from pathogens that could cross react with presumably pathogenic T cell lines from human patients with autoimmune disease (Oldstone, 1990). A sequence identity was recently found between an epitope in a Coxsackie virus protein and GAD65, suspected of being an autoantigen in diabetes. These peptides could reciprocally generate polyclonal T cell lines from mice that cross react with the other peptides (Tian, et al., 1994). No evidence, however, was provided that these peptides could stimulate clones from diabetic mice (or humans).

Recent developments in the field, in particular the identification of allele specific peptide binding motifs have transformed the field (Madden et al., 1991; Rotschke & Falk, 1991). Based on this knowledge, the structural basis for MHC linked susceptibility to autoimmune diseases can be reassessed at a level of detail sufficient for solving long-standing questions in the field. Motifs for peptide binding to several MHC class I and class II molecules have been defined by sequence analysis of naturally processed peptides and by mutational analysis of known epitopes. MHC class I bound peptides were found to be short (generally 8–10 amino acids long) and to possess two dominant MHC anchor residues; MHC class II bound peptides were found to be longer and more heterogeneous in size (Madden et al., 1991; Rotschke & Falk, 1991; Jardetzky et al. 1991, Chicz et al. 1993). Due to the size heterogeneity, however, it has proven more difficult to define MHC class II binding motifs based on sequence alignments. More recently, a crystal structure for HLA-DR1 demonstrated that there is a dominant hydrophobic anchor residue close to the N-terminus of the peptide and that secondary anchor residues are found at several other peptide positions (Brown et al., 1993). Even this work, however, could not provide a detailed description of the binding pockets of HLA-DR proteins, the particular residues involved in the formation of these pockets of the structural requirements or antigens for MHC binding.

Self-antigen epitope sequences, or autoreactive antigens, can be identified by a variety of techniques known in the art (see for example U.S. Pat. No. 5,874,531). Once a set of peptides has been identified, these peptides may optionally be screened for activity. The choice of such screens is at the discretion of the practitioner and beyond the scope of the present invention. Preferred screens, however, include in vitro tests for the ability to induce the proliferation of autoreactive T cells or to induce the secretion of lymphokines (cytokines) from these T cells or to induce other effector functions such as cytotoxicity. In some circumstances, human in vivo tests may be appropriate and in other circumstances animal models of the human disease may be available.

As used herein, the term "genetic construct" refers to the DNA or RNA molecule that comprises a nucleotide sequence which encodes the antigen or epitope and which includes initiation and termination signals operably linked to regulatory elements including a promoter and polyadenylation signal capable of directing expression in the cells of the vaccinated individual. As used herein, the term "expressible form" refers to gene constructs which contain the necessary regulatory elements operable linked to a coding sequence of a self-antigen epitope(s), such that when present in the cell of the individual, the coding sequence will be expressed. As used herein, the term "genetic vaccine" refers to a pharmaceutical preparation that comprises a genetic construct.

According to the present invention, DNA or RNA that encodes a self-antigen epitope(s) is introduced into the cells of an individual where it is expressed, thus producing the self-antigen epitope(s). The DNA or RNA is linked to regulatory elements necessary for expression in the cells of the individual. Regulatory elements include a promoter and a polyadenylation signal. In addition, other elements may also be included in the genetic construct.

The present invention provides genetic vaccines which comprise genetic constructs that contain DNA or RNA that encodes a self-antigen epitope(s). As used herein, the term "self-antigen epitope(s)" refers to a peptide or protein against which an immune response can be elicited. The self-antigen epitope(s) is an immunogenic peptide protein fragment or protein derived from an autoreactive antigen or a cell involved in autoimmune disease. The immune response directed against the epitope or protein will protect the individual against the specific infection or disease with which the self-antigen epitope(s) is associated.

The genetic construct of genetic vaccines comprise a nucleic acid sequence that encodes a self-antigen epitope(s) operably linked to regulatory elements needed for gene expression. Accordingly, incorporation of the DNA or RNA molecule into a living cell results in the expression of the DNA or RNA encoding the peptide or protein and thus, production of the self-antigen epitope(s).

When taken up by a cell, the genetic construct which includes the nucleotide sequence encoding the self-antigen epitope(s) linked to the regulatory elements may remain present in the cell as a functioning episomal molecule or it may integrate into the cell's chromosomal DNA. DNA may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Since integration into the chromosomal DNA necessarily requires manipulation of the chromosome, it is preferred to maintain the DNA construct as an episome. This reduces the risk of damaging the cell by splicing into the chromosome without affecting the effectiveness of the vaccine. Alternatively, RNA may be administered to the cell.

The necessary elements of a genetic construct of a genetic vaccine include a nucleic acid sequence that encodes a self-antigen epitope(s) and the regulatory elements necessary for expression of that sequence in the cells of the vaccinated individual. The regulatory elements are operably linked to the DNA sequence that encodes the self-antigen epitope(s) to enable expression. The nucleic acid sequence that encodes the self-antigen epitope(s) may be cDNA, genomic DNA, synthesized DNA or a hybrid thereof or an RNA molecule such as mRNA. Accordingly, as used herein, the terms "DNA construct", "genetic construct" and "nucleotide" or "nucleic acid" sequence are meant to refer to both DNA and RNA.

The regulatory elements necessary for gene expression include: a promoter, an initiation codon, a stop codon, and a polyadenylation signal. It is necessary that these elements be operable in the vaccinated individual. Moreover, it is necessary that these elements be appropriately linked to the nucleic acid sequence that encodes the self-antigen epitope (s) such that the nucleic acid sequence can be expressed in the cells of a vaccinated individual and thus the self-antigen epitope(s) can be produced.

Initiation codons and stop codon are generally considered to be part of a nucleic acid sequence that encodes the self-antigen epitope(s). It is necessary that these elements are functional in the vaccinated individual. Similarly, promoters and polyadenylation signals used must be functional within the cells of the vaccinated individual.

Examples of promoters useful to practice the present invention, especially in the production of a genetic vaccine for humans, include but are not limited to Mouse Mammary Tumor Virus (MMTV) promoter, Human Immunodeficiency Virus Long Terminal Repeat (HIV LTR) promoter, Moloney virus, ALV, Cytomegalovirus (CMV) promoter, human Actin, human Myosin, RSV, human Hemoglobin, human muscle creatine and EBV.

Examples of polyadenylation signals useful to practice the present invention, especially in the production of a genetic vaccine for humans, include but are not limited to SV40 polyadenylation signal and LTR polyadenylation signals.

In addition to the regulatory elements required for DNA expression, other elements may also be included in the DNA molecule. Such additional elements include enhancers. The enhancer may be selected from the group including but not limited to: human Actin, human Myosin, CMV, RSV, human Hemoglobin, human muscle creatine and EBV.

Genetic constructs can be provided with mammalian origin or replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EBNA-1 coding region which produces high copy episomal replication without integration.

In the present invention, the sequences encoding for at least one epitope from a self-antigen are inserted into a recombinant expression vector. The term "recombinant expression vector" refers to a plasmid, virus or other vehicle known in the art that has been manipulated by insertion or incorporation of the epitope genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene, 56:125, 1987), the pMSXND expression vector for expression in mammalian cells (Lee and Nathans, J. Biol. Chem., 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

Methods which are well known to those skilled in the art can be used to construct expression vectors containing the epitope coding sequence and appropriate transcriptional/translational control signals. These methods include in vitro recombinant DNA techniques, synthetic techniques, and in vivo recombination/genetic techniques. See, for example, the techniques described in Maniatis, et al., 1989 Molecular Cloning A Laboratory Manual, Cold Spring Harbor Laboratory, N.Y.

A variety of host-expression vector systems may be utilized to test for expression of the epitope coding sequence. These include but are not limited to microorganisms such as bacteria transformed with recombinant bacteriophage DNA, plasmid DNA or cosmid DNA expression vectors containing the epitope coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence; insect cell systems infected with recombinant virus expression vectors (e.g., baculovirus) containing the coding sequence; or animal cell systems infected with recombinant virus expression vectors (e.g., retroviruses, adenovirus, vaccinia virus) containing the coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see e.g., Bitter, et al., Methods in Enzymology 153:516–544, 1987). For example, when cloning in bacterial systems, inducible promoters such as pL of bacteriophage gamma., plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g. the retrovirus long terminal repeat; the adenovirus late promoter; the CMV vaccinia virus 7.5K promoter) may be used. Promoters produced by recombinant DNA or synthetic techniques may also be used to provide for transcription of the inserted coding sequence.

An additional element may be added which serves as a target for cell destruction if it is desirable to eliminate cells receiving the genetic construct for any reason. A herpes thymidine kinase (tk) gene in an expressible form can be included in the genetic construct. When the construct is introduced into the cell, tk will be produced. The drug gangcyclovir can be administered to the individual and that drug will cause the selective killing of any cell producing tk. Thus, a system can be provided which allows for the selective destruction of vaccinated cells.

In order to be a functional genetic construct, the regulatory elements must be operably linked to the nucleic acid sequence that encodes the target protein. Accordingly, it is necessary for the promoter and polyadenylation signal to be in frame with the coding sequence. In order to maximize protein production, regulatory sequences may be selected which are well suited for gene expression in the vaccinated cells. Moreover, codons may be selected which are most efficiently transcribed in the vaccinated cell. One having ordinary skill in the art can produce DNA constructs which are functional in vaccinated cells.

In order to test expression, genetic constructs can be tested for expression levels in vitro using tissue culture of cells of the same type as those to be vaccinated. For example, if the genetic vaccine is to be administered into human muscle cells, muscle cells grown in culture such as solid muscle tumors cells of rhabdomyosarcoma may be used as an in vitro model to measure expression level.

The present invention provides a method of treating individuals suffering from autoimmune diseases and disorders by conferring a broad based protective immune response against targets that are associated with autoimmunity including cell receptors and "self"-directed antibodies.

T cell mediated autoimmune diseases include Rheumatoid arthritis (RA), multiple sclerosis (MS), Sjogrens, sarcoidosis, insulin dependent diabetes mellitus (IDDM), autoimmune thyroiditis, reactive arthritis, ankylosing sponduilitis, scleroderma, panmyositis, dermatomyositis, psorisis, vasculitis, Wegner's granulomatosis, Crohn's disease and colitis. Each of these diseases is most likely characterized by high affinity T cell receptors that bind to endogenous antigens and initiate the inflammatory cascade associated with autoimmune diseases. Vaccination against the variable region of the high affinity T cells would elicit an immune response including CTLs to eliminate those T cells. The methods and compositions of the invention are useful for treating any of these or other autoimmune diseases.

In RA, several specific variable regions of T cell receptors (TCRs) which are involved in the disease have been characterized. These TCRs include Vbeta-3, beta-14, Vbeta-17 and Valpha-28. Thus, vaccination with a DNA construct that encodes at least one of these proteins will elicit an immune response that will target T cells involved in RA. See: Howell, M. D., et al., 1991 Proc. Natl. Acad. Sci. USA 88:10921–10925; Paliard, X., et al., 1991 Science 253:325–329; Williams, W. V., et al., 1992 J. Clin. Invest. 90:326–333; each of which is incorporated herein by reference. In addition, epitopes from collagen may be useful in the genetic constructs or methods of immunization of the present invention.

In MS, several specific variable regions of TCRs which are involved in the disease have been characterized. These TCRs include Vbeta-7 and Valpha-10. Thus, vaccination with a DNA construct that encodes at least one of these proteins will elicit an immune response that will target T cells involved in MS. See: Wucherpfennig, K. W., et al., 1990 Science 248:1016–1019; Oksenberg, J. R., et al., 1990 Nature 345:344–346; each of which is incorporated herein by reference. Candidate antigens for the methods of the invention also include myelin basic protein, proteolipid protein, transaldolase, 2'3' cyclic nucleotide 3' phosphodiesterase, myelin oliodendroglial glycoprotein and myelin-associated glycoprotein.

In scleroderma, several specific variable regions of TCRs which are involved in the disease have been characterized. These TCRs include Vbeta-6, Vbeta-8, Vbeta-17 and Valpha-16. Thus, vaccination with a DNA construct that encodes at least one of these proteins will elicit an immune response that will target T cells involved in scleroderma.

B cell mediated autoimmune diseases include Lupus (SLE), Grave's disease, myathon, myasthinia gravas, autoimmune hemolytic anemia, autoimmune thrombocytopenia, asthma, cryobulinemia, primary biliary sclerosis and pernias anemia. Each of these diseases is characterized by antibodies which bind to endogenous antigens and initiate the inflammatory cascade associated with autoimmune diseases.

In the case of SLE, the antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

In the case of IDDM, antigens include the insulin B chain or partial or whole insulin, glutamic acid decarboxylase (GAD65/67), islet cell antigens (IAs)- and heat shock protein (HSP60). In a preferred embodiment, as illustrated herein, insulin B chain is utilized in the genetic construct for vaccination purposes.

With respect to the constructs of the present invention, one or more epitopes of the self antigen will be expressed by the host following transfection or transformation of autologous cells with the administered genetic material. The expressed epitope or epitopes then elicit the desired immune response in the subject. As previously discussed, it will be appreciated that the disclosed constructs may be administered in the form of naked recombinant molecules (e.g. DNA or RNA) associated with a pharmaceutically acceptable carrier or in any one of a number of more elaborate vector forms. In either case, nucleic acids compatible with the invention will preferably encode one or more epitopes, and may optionally further comprise elements that regulate the expression and/or stability and/or immunogenicity of the epitope.

To provide enhanced stability and/or immunogenicity of the relevant epitope, it may be desirable to present the epitope in the context of a larger peptide or protein. For example, the relevant may be expressed in the variable region of a chimeric antibody or as a domain of the selected self-antigen. In other preferred embodiments, it may be advantageous to administer a full-length protein (e.g. myelin basic protein in the case of multiple sclerosis) comprising one or more epitopes. Alternatively, it may be desirable to administer compositions comprising combinations or cocktails of genetic material encoding various immunogenic self-epitopes and/or cofactors. In this regard, it will be appreciated that the relevant epitopes may be derived from the same or different self-antigens. As explained above, the selected epitopes may be derived from self-antigens that are critical to the pathogenesis of the subject disease or from immunogenic host peptides that play no part of the etiology of the disorder. In addition to the broad target range, the disclosed compositions may comprise various epitope combinations. For example, the compositions of the present invention may comprise genetic material encoding peptides or proteins comprising mixtures of B cell epitopes, mixtures of T cell epitopes, or combinations of B and T cell epitopes.

More particularly, administration of compositions that comprise or express more than one relevant epitope may exhibit an unexpected synergistic effect. It will be appreciated that such combinations may prove to be more efficient at conferring the desired immunomodulation with respect to autoreactive cells than compositions comprising a single nucleic acid species encoding a single relevant epitope. Those skilled in the art will further appreciate that such synergism could allow for effective immunoprophylactic or immunotherapeutic responses to be generated with lower dosing and less frequent administration than single-epitope compositions. Moreover, the use of such multi-epitope compositions may provide more comprehensive protection as the induced multi-site immunity would tend to be more resistant to natural phenotypic variation within a species or rapid mutation of a target antigen by the selected pathogen. Of course, effective immunity may also be imparted by constructs encoding a single B or T cell epitope and such compounds and compositions are clearly contemplated as being within the scope of the present invention.

According to the invention, the genetic vaccine may be administered directly into the individual to be immunized or ex vivo into removed cells of the individual which are reimplanted after administration. By either route, the genetic material is introduced into cells which are present in the body of the individual. Preferred routes of administration include intramuscular, intraperitoneal, intradermal and subcutaneous injection. Alternatively, the genetic vaccine may be introduced by various means into cells that are removed from the individual. Such means include, for example, transfection, electroporation and microprojectile bombardment. After the genetic construct is taken up by the cells, they are reimplanted into the individual. It is contemplated that otherwise non-immunogenic cells that have genetic constructs incorporated therein can be implanted into the individual even if the vaccinated cells were originally taken from another individual.

The genetic vaccines according to the present invention comprise about 0.1 to about 1000 or about 10 mg of DNA. In some preferred embodiments, the vaccines contain about 1 to about 500 micrograms of DNA. In some preferred embodiments, the vaccines contain about 25 to about 250 micrograms of DNA. Most preferably, the vaccines contain about 100 micrograms DNA.

The genetic vaccines according to the present invention are formulated according to the mode of administration to be used. One having ordinary skill in the art can readily formulate a genetic vaccine that comprises a genetic construct. In cases where intramuscular injection is the chosen mode of administration, an isotonic formulation is used. Generally, additives for isotonicity can include sodium chloride, dextrose, mannitol, sorbitol and lactose. Isotonic solutions such as phosphate buffered saline are preferred. Stabilizers include gelatin and albumin.

According to the present invention, prior to or contemporaneously with administration of the genetic construct, cells may be administered a "cell stimulating" or "cell proliferative" agent. As used herein, the terms "cell stimulating agent" or "cell proliferative agent" are used interchangeably and refer to compounds which stimulate cell division. Such compounds facilitate DNA and RNA uptake.

For example, bupivcaine, well known and commercially available pharmaceutical compound, is administered prior to or contemporaneously with the genetic construct. Bupivacaine is related chemically and pharmacologically to the aminoacyl class of local anesthetics. It is a homologue of mepivacaine and related to lidocaine. Bupivacaine renders muscle tissue voltage sensitive to sodium challenge and effects ion concentration within the cells. A complete description of bupivacaine's pharmacological activities can be found in Ritchie, J. M. and N. M. Greene, The Pharmacological Basis of Therapeutics, Eds.: Gilman, A. G. et al, 8th Edition, Chapter 15:3111, which is incorporated herein by reference. Compounds that display a functional similarity to bupivacaine may be useful in the method of the present invention.

In addition to bupivacaine, mepivacaine, lidocaine and other similarly acting compounds, other contemplated cell stimulating agents include lectins, growth factors, cytokines and lymphokines such as platelet derived growth factor (PDGF), GCSF, GMCSF, epidermal growth factor (EGF) and IL-4.

Bupivacaine-HCl is chemically designated as 2-piperidinecarboxamide, 1-butyl-N-(2,6-dimethylphenyl)-monohydrochloride, monohydrate and is widely available commercially for pharmaceutical uses from many sources including from Astra Pharmaceutical Products Inc. (Westboro, Mass.) and Sanofi Winthrop Pharmaceuticals (New York, N.Y.), Eastman Kodak (Rochester, N.Y.). About 50 ul to about 2 ml of 0.5% bupivacaine-HCl and 0.1% methylparaben in an isotonic pharmaceutical carrier may be administered to the site where the vaccine is to be administered, preferably, 50 ul to about 1500 ul, more preferably about 1 ml. The genetic construct may be combined with collagen as an emulsion and delivered intraperatonally. The collagen emulsion provides a means for sustained release of DNA. 50 ul to 2 ml of collagen are used. About 100 ug DNA are combined with 1 ml of collagen in a preferred embodiment using this formulation.

In some embodiments of the invention, the individual is first subject to bupivacaine injection prior to genetic vaccination by intramuscular injection. That is, up to, for example, about 24 hrs prior to vaccination, the individual is first injected with bupivacaine. Alternatively, bupivacaine can be injected simultaneously, minute before or after vaccination.

In some embodiments of the invention, the individual is subject to a series of vaccinations to produce a full, broad immune response. According to this method, at least two and preferably four injections are given over a period of time. The period of time between injections may include from 24 hours apart to two weeks or longer between injections, preferably one week apart. Alternatively, at least two and up to four separate injections are given simultaneously at different parts of the body.

While the disclosure herein primarily relates to uses of the methods of the present invention to immunize humans, the methods of the present invention can be applied to veterinary medical uses too. It is within the scope of the present invention to provide methods of immunizing non-human as well as human individuals against pathogens and protein specific disorders and diseases. Accordingly, the present invention relates to genetic immunization of mammals, birds and fish. The methods of the present invention can be particularly useful for mammalian species including human, bovine, ovine, porcine, equine, canine and feline species.

While this disclosure generally discusses immunization in the context of prophylactic methods of protection, the term "immunizing" is meant to refer to both prophylactic and therapeutic methods. Thus, a method of immunizing includes both methods of protecting an individual from pathogen challenge or occurrence or proliferation of specific cells as well as methods of treating an individual suffering from pathogen infection, or autoimmune disease. Accordingly, the present invention may be used as a vaccine for prophylactic protection or in a therapeutic manner; that is, as immunotherapeutic methods and preparations.

Various viral vectors which can be utilized for administration to a subject as taught herein include adenovirus, adeno-associated virus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Most preferably, a non-human primate retroviral vector is employed, such as the gibbon ape leukemia virus (GaLV), thereby providing a broader host range than murine vectors in humans, for example.

A number of additional retroviral vectors can incorporate multiple genes. All of these vectors can transfer or incorporate a gene for a selectable marker so that transduced cells can be identified and generated. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the coding sequences.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include but are not limited to .PSI.2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Another targeted delivery system for delivering a genetic construct of the invention is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 um can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci., 6:77, 1981). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes has been classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

In general, the compounds bound to the surface of the targeted delivery system will be ligands and receptors which will allow the targeted delivery system to find and "home in" on the desired cells. A ligand may be any compound of interest which will bind to another compound, such as a receptor.

Biological response modifiers (BRM's) stimulate the immune system without specificity. Experimentation in their use dates to the 19th century observation that infectious empyemas occassionally led to resolution of a tumor. William Coley reasoned in the late nineteenth century that tumors would be viewed as foreign if the immune system was sufficiently activated; he subsequently developed a collection of heat-killed bacteria with which to treat cancer patients. The property of non-specific immune stimulation is shared by BRM's and adjuvants. Indeed, the terms are in this sense interchangeable.

With respect to cancer immunotherapy, two types of BRM stand out: BCG and cytokines. BCG (Bacille de Calmette et Guerin) is a live attenuated bovine tubercle bacillus possessing nonspecific, immunostimulating properties. It is now F.D.A. approved for use as a prophylactic measure against tumor recurrence following endoscopic resection of superficial bladder cancer. Intravesical instillation is thought to lead to tumor cell killing by either macrophages or T lymphocytes. The response to BCG is immunologically non-specific in that it seems to involve a general activation of the immune system. Efficacy is dependent on both a limited tumor burden and patient immunocompetence.

Similarly, cytokines lead to lymphocyte activation by virtue of altering the cellular environment of antigen presentation. They can thus act as adjuvants for tumor antigens presented by whole tumor cells, tumor cell lysates, or specific tumor cell antigens. The specific antigen presented with cytokines must still carry its own helper T cell epitopes in order to stimulate a high titer B cell (antibody) response.

Several cytokines have shown promise for treatment of cancer. Alpha-interferon is F.D.A. approved for treatment of hairy cell leukemia. GM-CSF and IL-2 have also received favorable attention. GM-CSF supports proliferation of polymorphonuclear granulocytes (neutrophils) and monocytes, in addition to activating mature cells of the same lineages to become tumoricidal and phagocytic in vitro. IL-2 stimulates proliferation and activation of T lymphocytes.

The suitable immunopotentiating agents or biological response modifiers include agents that may not be immunogenic to the host, but nevertheless potentiate immunity by activating or enhancing the activity of cells of the immune system, such as T lymphocytes, natural killer cells, or lymphokine activated killer (LAK) cells. Included in this category of immunopotentiating agents are those encoding a number of the cytokines classified as "interleukins". These include, for example, interleukins 1 through 12. Also included in this category, although not necessarily working according to the same mechanisms, are interferons, and in particular gamma interferon (.gamma.-IFN), tumor necrosis factor (TNF) and granulocyte-macrophage-colony stimulating factor (GM-CSF).

By the term "cytokine" or grammatical equivalents, herein is meant the general class of hormones of the cells of the immune system, both lymphokines and monokines, and others. The definition is meant to include, but is not limited to, those hormones that act locally and do not circulate in the blood, and which, when used in accord with the present invention, will result in an alteration of an individual's immune response. The cytokine can be, but is not limited to, IL-1(.alpha. or beta), IL-2, IL-3, IL-4, IL-5, IL-6, IL-7, IL-8, IL-9, IL-10, IL-11, IL-12, GM-CSF, M-CSF, G-CSF, LIF, LT, TGF-beta gamma-IFN (or .alpha. or .beta.-IFN), TNF-.alpha., BCGF, CD2, or ICAM. Descriptions of the aforementioned cytokines as well as other applicable immunomodulatory agents may be found in "Cytokines and Cytokine Receptors", A. S. Hamblin, 1993, (D. Male, ed., Oxford University Press, New York, N.Y.), or the "Guidebook to Cytokines and Their Receptors", 1995, N. A. Nicola, ed. (Oxford University Press, New York, N.Y.) herein incorporated by reference.

Where therapeutic use in humans is contemplated, the cytokines or hormones will preferably be substantially similar to the human form of the protein or have been derived from human sequences (i.e., of human origin).

Additionally, cytokines of other mammals with substantial homology to the human forms of IL-2, GM-CSF, TNF-alpha, and others, will be useful in the invention when demonstrated to exhibit similar activity on the immune system. Similarly, proteins that are substantially analogous to any particular cytokine, but have relatively minor changes of protein sequence, will also find use in the present invention. It is well known that some small alterations in protein sequence may be possible without disturbing the functional abilities of the protein molecule, and thus proteins can be made that function as cytokines in the present invention but differ slightly from currently known sequences. Thus, proteins that are substantially similar to any particular cytokine, but have relatively minor changes of protein sequence, will also find use in the present invention.

Finally, the use of either the singular or plural form of the word "cytokine" or "chemokine" or "interferon" or "interleukin" in this application is not determinative and should not limit interpretation of the present invention and claims.

Whatever form of immunomodulating agent selected the compositions of the present invention may be formulated to provide desired stability and facilitate the selected form of administration. For example, the compositions may be administered using all conventional routes known in the art including, but not limited to, oral, vaginal, aural, nasal, pulmonary, intravenous, intracranial, intraperitoneal, subcutaneous, or intramuscular administration. Within other embodiments of the invention, the compositions described herein may be administered as part of a sustained release implant. Within yet other embodiments, compositions of the present invention may be formulated as a lyophilizate or spray dried formulation, utilizing appropriate art recognized excipients that provide stability prior to rehydration.

Preparations for parenteral administration are contained in a "pharmaceutically acceptable carrier". Such carriers include sterile aqueous or non-aqueous solutions, suspensions and emulsions. Examples of non-aqueous solvents include propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, and inert gases and the like.

As applied in the present invention, the term "pharmaceutically active substance" encompasses any substance that will produce a therapeutically beneficial pharmacological response when administered to a host, including both humans and animals. More than one pharmaceutically active substance may be included, if desired, in a pharmaceutical composition used in the method of the present invention.

The pharmaceutically active substance can be employed in the present invention in various forms, such as molecular complexes or pharmaceutically acceptable salts. Representative examples of such salts are succinate, hydrochloride, hydrobromide, sulfate, phosphate, nitrate, borate, acetate, maleate, tartrate, salicylate, metal salts (e.g., alkali or alkaline earth), ammonium or amine salts (e.g., quaternary ammonium) and the like. Furthermore, derivatives of the active substances such as esters, amides, and ethers which have desirable retention and release characteristics but which are readily hydrolyzed in vivo by physiological pH or enzymes can also be employed.

As used herein, the term "therapeutically effective amount" or an "immunomodulatory effective amount" means that the amount of the pharmaceutically active substance is of sufficient quantity and activity to induce desired pharmacological effect which, in the present invention, is the immunopotentiation of an immune response to an epitope of a self-antigen. The amount-of substance can vary greatly according to the effectiveness of a particular active substance, the age, weight, and response of the individual host as well as the nature and severity of the host's symptoms. Accordingly, there is no upper or lower critical limitation upon the amount of the active substance. The required quantity to be employed in the present invention can readily be determined by those skilled in the art.

By the term "regulating the immune response" or grammatical equivalents, herein is meant any alteration in any cell type involved in the immune response. The definition is meant to include an increase or decrease in the number of cells, an increase or decrease in the activity of the cells, or any other changes which can occur within the immune system. The cells may be, but are not limited to, T lymphocytes, B lymphocytes, natural killer (NK) cells, macrophages, eosinophils, mast cells, dendritic cells, or neutrophils. The definition encompasses both a stimulation or enhancement of the immune system to develop a sufficiently potent response to a deleterious target, as well as a suppression of the immune system to avoid a destructive response to a desirable target. In the case of stimulation of the immune system, the definition includes future protection against subsequent challenge (e.g., with a virus).

By the term "epitope" or "antigen" from a self-antigen or grammatical equivalents thereof, herein is meant any protein, carbohydrate or other component capable of eliciting an immune response. The definition is meant to include, but is not limited to, using at least one epitope.

By the term "systemic immune response" or grammatical equivalents herein, is meant an immune response which is not localized, but affects the individual as a whole, thus allowing specific subsequent responses to the same stimulus.

By the term "co-administering" or grammatical equivalents herein, is meant a process whereby at least one self-antigen epitope and at least one cytokine or other biological response modifier are encountered by the individual's immune system at essentially the same time. The components need not be administered by means of the same vehicle. If they are administered in two separate vehicles, they must be administered sufficiently closely, both in time and by route of administration, that they are encountered essentially simultaneously by the individual's immune system to achieve the desired specificity. It should be understood that the at least one epitope and at least one biological response modifier can be encoded on the same genetic construct or on more than one construct that is co-administered (e.g., same or different plasmids).

One of ordinary skill will appreciate that, from a medical practitioner's or patient's perspective, virtually any alleviation or prevention of an undesirable symptom (e.g., symptoms related to disease, sensitivity to environmental or factors, normal aging, and the like) would be desirable. Thus, for the purposes of this Application, the terms "treatment", "therapeutic use", or "medicinal use" used herein shall refer to any and all uses of the claimed compositions which remedy a disease state or symptoms, or otherwise prevent, hinder, retard, or reverse the progression of disease or other undesirable symptoms in any way whatsoever.

An appropriate dosage of genetic construct, may be determined by any of several well established methodologies. For instance, animal studies are commonly used to determine the maximal tolerable dose, or MTD, of bioactive agent per kilogram weight. In general, at least one of the animal species tested is mammalian. Those skilled in the art regularly extrapolate doses for efficacy and avoiding toxicity to other species, including human. Before human studies of efficacy are undertaken, Phase I clinical studies in normal subjects help establish safe doses. Alternatively, initial toxicity studies may involve individuals that are at the terminal stages of the disease progression.

By the term "subject" or "individual" or grammatical equivalents herein is meant any one individual.

These novel vaccine formulations can be administered in conventional solid or liquid pharmaceutical administration forms, e.g. uncoated or (film-) coated tablets, capsules, powders, granules, suppositories, or solutions. These are produced in a conventional manner. The active substances can for this purpose be processed with conventional pharmaceutical aids such as tablet binders, fillers, preservatives, tablet disintegrants, flow regulators, plasticizers, wetting agents, dispersants, emulsifiers, solvents, sustained release compositions, antioxidants and/or propellent gases (cf. H. Sucker, et al. "Pharmazeutische Technologie". 1978. Thieme-Verlag, Stuttgart). The administration forms obtained in this way normally contain 1–90% by weight of the active substance.

As previously alluded to, the immunomodulating compounds or constructs of the present invention will preferably be in the form of a recombinant nucleotide that provides for expression of the selected epitope or epitopes or self-antigen. In accordance with the teachings herein, the construct may be administered as a circular or linearized plasmid in conjunction with a pharmaceutically acceptable carrier or may be associated with a more elaborate vector. For example, the constructs of the present invention may be administered in the form of naked DNA, viral vectors, recombinant phages, transformed bacteria or transformed host cells or heterologous cells. Such vector systems are well within the purview of the skilled artisan and may easily be provided without undue experimentation in view of the instant specification. Besides being compatible with a number of delivery systems, the constructs of the instant invention may be used treat a variety of autoimmune disorders including, for example, multiple sclerosis, lupis, rheumatoid arthritis, myastenia gravis, scleroderma, insulin-dependent diabetes and ulcerative colitis.

Regardless of the epitope selected or the ultimate form in which it is delivered, (i.e. plasmids, viral vector, etc.), those skilled in the art will further appreciate that the effective treatment or induction of prophylaxis in a subject may include more than one inoculation. As used herein, these terms and related nomenclature refer to the down regulation of autoreactive immune cells through the induction of appropriate biological response modifiers by the expressed self-epitope. It will be appreciated that the treatment or prevention of an autoimmune disorder does not require that the entire population of autoreactive cells be completely eliminated but rather that the population be reduced or anergized to the point of providing clinically beneficial effects. Besides a reduction in the severity of symptoms associated with a given autoimmune disorder, assays for quantitating autoreactive responses are well known and could easily be performed by those skilled in the art.

Similarly, the term "inoculating", as used herein, refers to administering or introducing a pharmaceutically acceptable composition incorporating an immunomodulating compound comprising at least one self-epitope that is capable of being expressed by the inoculated host. While an effective immune response may be induced with a single inoculation, the treatment of a subject may comprise multiple inoculations or a subsequent booster or boosters. As such, the methods of the present invention may comprise one, two, three, four or even five inoculations in order to achieve the desired immunoprophylactic effect. Those skilled in the art will further appreciate that the compositions of the present invention may be used to inoculate neonates (0–6 mo), infants (6 mo–2 yr), children (2 yr–13 yr) or adults (13 yr +).

Such antigens may be whole self-antigens, antigen fragments (obtained by molecular biology or biochemical techniques well known in the art) or peptides comprising single epitopes. The expressed epitopes may be associated with other natural products such as immunoglobulins or any natural or synthetic ligand for receptors on body cells. They may be administered as isolated, individual components or in mixtures. Examples for expressed epitopes that may be useful in the treatment of diabetes type I include, but are not limited to, such peptides and antigens as: GAD65 (glutamic acid decarboxylase 65—Baekkeskov et al., Nature 1990, 347:151), insulin (Palmer et al., Science 1983, 222:1337), ICA512/IA-2 (islet cell antigen 512; Rabin et al., J. Immunol. 1994, 152:3183). In the case of MS, such proteins and peptides are: MBP (myelin basic protein, Steinman et al., 1995, Mol. Med. Today, 1:79; Warren et al., 1995, Proc. Natl. Acad. Sci. USA, 92:11061). PLP. transaldolase, 2',3' cyclic nucleotide 3' phosphodiesterases (CNP), MOG and MAG (Steinman L., 1995, Nature, 375:739). Besides autoimmune diseases, it will be appreciated that the compositions and methods of the present invention may also be used to down regulate immune responses provoked by allergens.

Certain peptides and proteins are known to have to ability to modulate or down-regulate immune responses to self-antigens. Such peptides or proteins may act by engaging endogenous receptors leading to activation or inhibition of certain processes, or by interfering with the ligand-receptor binding of endogenous elements. Examples of such biological response modifiers that exert immune modulatory function leading to suppression of autoimmunity include, but are not limited to, IL-4, IL-10, IL-13, IL-9, native or in the form of fragments attached, incorporated or complexed with other molecules including the self-eptopes disclosed herein. In this regard, the current invention advantageously permits for co-formulation of a selected antigen or epitope with cofactors that might augment stimulation local immune responses within the targeted delivery site. By enhancing the localized immune response through the use of such coexpressed cofactors, the constructs of the present invention provide for increased down regulation of the autoreactive entities.

Other active proteins or peptides that may be used in accordance with the present invention comprise chemokines in native form or as fragments, constructs or complexes with other molecules which may modulate or inhibit the recruitment of lymphocytes. For example MIG, IP-10, MIP-1, MIP-1β and RANTES are thought to mediate the recruitment of Th1 cells (Sallusto et al., 1998, J. Exp. Med., 187:875; Ward et al., 1998, Immunity, 9:1). Similarly, cytokine or chemokine receptors in native form, or as fragments, recombinant constructs or complexes with other molecules may inhibit the recruitment or activation of certain lymphocytes. Examples of cytokine and chemokine receptors that are likely to inhibit ongoing Th1 responses comprise the IL-12 receptor, IFN-γ receptor, IL-2 receptor, TNF-α receptor, CXCR3 or CCR5. Of course, it will be appreciated that compatible compounds are not limited to cytokines, chemokines or their receptors, but may include other ligands or receptors (in native form, fragments, constructs or complexes with other molecules) like integrins and homing receptors. In preferred embodiments all these categories of compounds may be formulated and administered either locally or systemically in order to suppress or modulate undesirable autoreactivity.

As discussed above, the compositions, compounds and methods of the present invention may be particularly useful for reducing autoreactivity in neonatal or infant mammals thereby preventing or reducing future autoimmunity. The term "infant" as used herein, refers to a human or non-human mammal during the period of life following birth wherein the immune system has not yet fully matured. In humans, this period extends from birth to the age of about nine months while in mice, this period extends from birth to about four weeks of age. The terms "newborn" and "neonate" refer to a subset of infant mammals which have essentially just been born. Other characteristics associated with "infants" according to the present invention include an immune response which has (i) susceptibility to high zone tolerance (deletion/anergy of T cell precursors, increased tendency for apoptosis); (ii) a Th2 biased helper response (phenotypical particularities of neonatal T cells; decreased CD40L expression on neonatal T cells); (iii) reduced magnitude of the cellular response (reduced number of functional T cells; reduced antigen-presenting cell function); and (iv) reduced magnitude and restricted type of humoral response (predominance of IgMhigh, IgDlow, B cells, reduced cooperation between Th and B cells). In specific nonlimiting embodiments of the invention, the disclosed immunomodulating constructs may be administered to an infant mammal wherein maternal antibodies remain present in detectable amounts. In a related embodiment, the pregnant mother may be inoculated with the disclosed compositions so as to produce the desired immunoregulation in the fetus.

Presentation of the following non-limiting Examples will serve to further illustrate the principles of the present invention. In this regard, a list of abbreviations and corresponding definition used throughout the following discussion and the Examples is provided:

LCMV: lymphocytic chiromeningitis virus;
LCMV-NP or NP: lymphocytic chiromeningitis virus nucleoprotein;
RIP-LCMV-NP: transgenic mouse line that expresses LCMV-NP under control of the rat insulin promoter (RIP);
IDDM: insulin-dependent diabetes mellitus;
pCMV: a plasmid vector;
pCMV-insB: a plasmid vector encoding porcine insulin B-chain;
pCMV-NP: a plasmid vector encoding the nucleoprotein of LCMV;
pCTL: LCMV-specific CTL precursor.

For obvious practical and moral reasons, initial work in humans to determine the efficacy of experimental compositions or methods with regard to many diseases is infeasible. Thus, during early development of any drug it is standard procedure to employ appropriate animal models for reasons of safety and expense. The success of implementing laboratory animal models is predicated on the understanding that immunodominant epitopes are frequently active in different host species. Thus, an immunogenic determinant in one species, for example a rodent or pig, will generally be immunoreactive in a different species such as in humans. Only after the appropriate animal models are sufficiently developed will clinical trials in humans be carried out to further demonstrate the safety and efficacy of a vaccine in man. Accordingly, for purposes of explanation only and not for purposes of limitation, the present invention will be primarily demonstrated in the exemplary context of mice as the mammalian host. Those skilled in the art will appreciate that the present invention may be practiced with other mammalian hosts including humans and domesticated animals.

In this respect, the well established, art recognized RIP-LCMV-NP mouse model, which is used as an animal model for virally induced insulin-dependent diabetes mellitus, can be induced by infection with lymphocytic chiromeningitis virus (LCMV). Following infection with LCMV 90–100% of the mice routinely develop diabetes mediated by CD4$^+$ and CD8$^+$ lymphocytes which eliminate the viral infection and, at the same time, react with the LCMV nucleoprotein expressed by the murine β-cells. This model possesses two distinct advantages in that the disease trigger may be precisely controlled and the autoreactive (anti-NP) lymphocytes can be precisely tracked. Although the target antigen(s) in human diabetes is still debatable, the frequency of T cells specific for pancreatic β-cells are higher in IDDM patients than in normal subjects. Silencing those autoreactive T cells is therefore likely to be a logical approach to prevent or treat diabetes and, accordingly, this model will be used to illustrate the advantages of the present invention. However, it should be emphasized that the exemplified methods and compositions are applicable to a wide variety of autoimmune diseases and are in no way limited to any particular condition or disorder.

EXAMPLE I

Inoculation of Diabetic Transgenic Mice

In order to demonstrate the advantages of the present invention, inducible diabetic transgenic mice were obtained and vaccinated with the disclosed compositions. More particularly, the transgenic RIP-LCMV NP 25-3 H-$2^d$ mouse line used in the following Examples expresses the nucleoprotein (NP) of LCMV under control of the rat insulin promoter (RIP) in the pancreatic β-cells as well as in the thymus, but not in any other tissues. Balb/c non-transgenic H-$2^d$ mice were used as controls in some experiments (8). The virus used for induction of IDDM was LCMV Armstrong (ARM) strain (clone 53b). Four to 21 week old RIP-NP 25-3 mice were inoculated intraperitoneally (i.p.) with $1 \times 10^5$ pfu LCMV ARM in a volume of 0.2 ml.

Selected mice were orally innoculated with porcine insulin purified from pancreatic glands (Novo Nordisk, Bagsvaerd, Denmark) as well as other control peptides. Insulin was solubilized in acid buffer, pH adjusted and the solution stored at −20° C. until used. Peptides were synthesized on an automated peptide synthesizer (Applied Biosystems 430A) by the solid-phase method using t-butoxyl or N-(9-fluorenyl)methoxycarbonyl (Fmoc) chemistry, purified by high pressure liquid chromatography on a RP300-C8 reversed-phase column (Brownlee Lab) and identified by fast atom bombardment of electrospray mass spectrometry. LCMV was grown, purified and UV-inactivated while NP peptides were synthesized by the Scripps Core facility. All oral antigens were administered via a blunt-ended curved feeding tube inserted into the esophagus/stomach. RIP-NP mice were fed biweekly with 0.5 ml of an aqueous solution containing 1 mg/ml antigen. Feeding was started one week prior to infection with LCMV and discontinued after 8 weeks. Other control groups received saline or bovine serum albumin (BSA) at a concentration of 1 mg/ml.

As further controls, various mice were inoculated with insulin A and B polypeptides. Purified insulin A and B chains were obtained from Zymogenetics (Seattle, Wash.). For Immunizations RIP-NP (H-$2^d$) transgenic mice received 100 μg of B or A chain peptide in a 1:1 incomplete Freund's adjuvant (IFA) emulsion. Injections were given twice on days 2 and 8 post LCMV infection.

Figure 1:
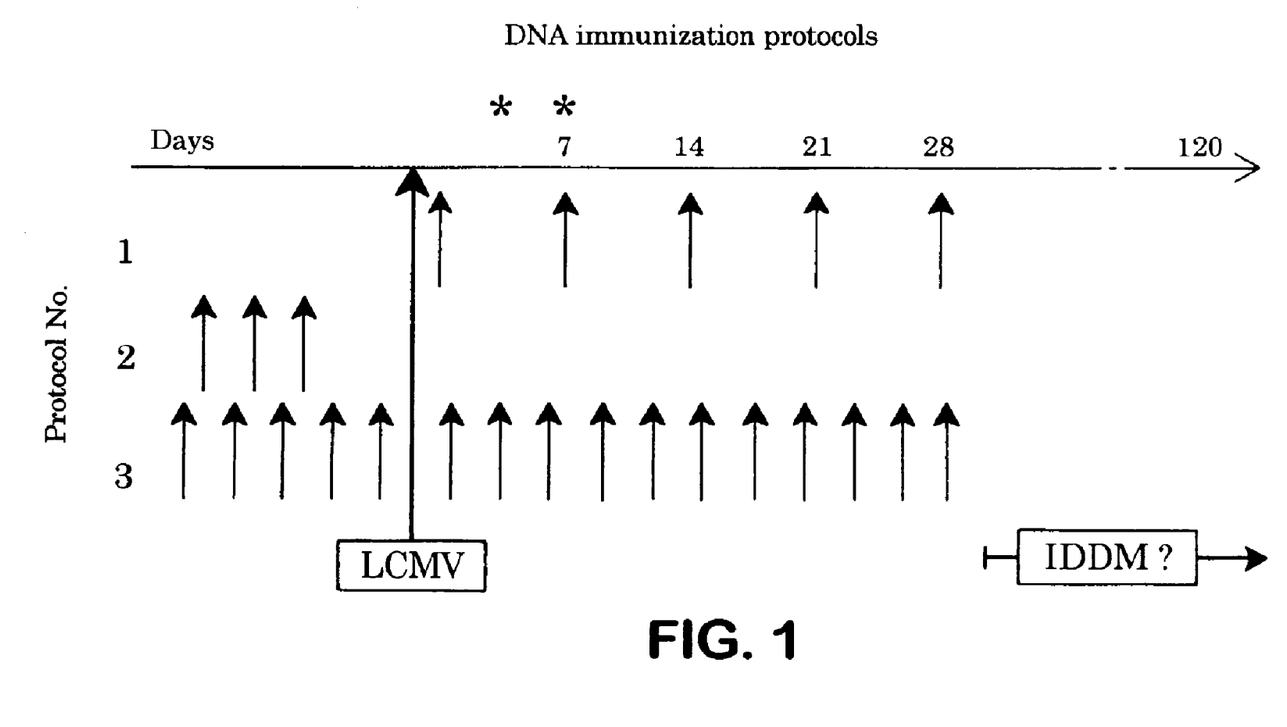

Still other mice were innoculated with immunomodulating constructs as described herein. To prepare the constructs and various controls, open reading frames encoding LCMV-NP or porcine insulin B-chain were placed into pCMV, a plasmid described previously (Yokoyama, M. et al. *J. Virol.* 69:2684–2688, which is incorporated herein by reference). DNA was prepared at a concentration of 1 mg/ml saline. 50 ml were injected into the quadriceps femoris muscle of each hind leg after shaving the fur and under general anesthesia using Metophane® anesthetic. On each occasion, injection was performed into both hind-legs (a total of 100 ml per mouse). Immunizations were given according to the protocols displayed in FIG. 1 and were continued for a maximum of 4 weeks post LCMV infection (protocols 1 and 3 of FIG. 1).

EXAMPLE II

Progression of Diabetes in Immunized and Non-Immunized Mice

Figure 2:
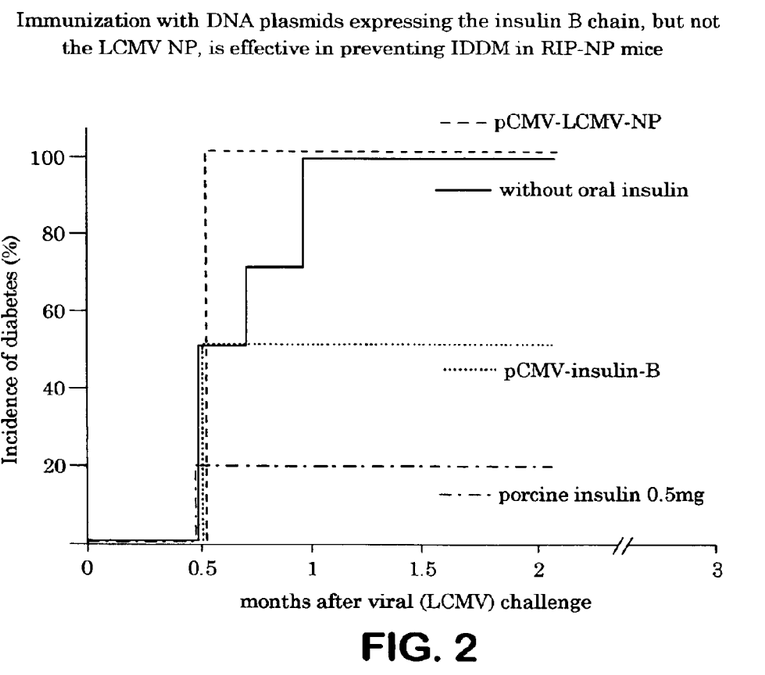

Blood samples from the immunized RIP-LCMV mice from Example I, along with non-immunized controls were screened for diabetes twice a week from 10 weeks of age by testing for hyperglycemia by blood glucose tests. Diabetes was defined by two consecutive blood glucose analyses (Accucheck III analyzer, Boehringer Mannheim, Indianapolis, Ind.) with values above 350 mg/dl. The results of this screening are shown in FIG. 2.

EXAMPLE III

Transfer of Splenocytes from Insulin-B Protected Mice Prevents IDDM

DNA-immunized mice were challenged with LCMV, and blood glucose levels were followed for 1 month to identify "protected" and "non-protected" mice. Splenocytes were harvested from "protected" mice (pCMV-ins-B immunized, protocol 1) or from "non-protected" mice (PCMV-NP immunized, protocol 1 or 2), and were cultured in vitro with the antigen stimulus shown above. After 3 days of culture, IL-4 and IFN-γ levels in tissue culture supernatants were determined by ELISA as follows:

Cytokines (IL-4, IFN-γ) produced by splenocytes were detected using the ELISA (Pharmingen, San Diego, Calif.) assay. Briefly, 96-well Millititer™ HA plates (Millipore, Bedford, Mass.) were coated with the respective capture antibodies for IL-4 and IFN-γ diluted to 2 μg/ml. After overnight incubation at 4° C., plates were washed 4 times with PBS-TWEEN 20 (0.05%) and pre-incubated with PBS containing 10% FCS for 1 hour at RT. Tissue culture supernatants and standards were added at various dilutions in PBS with 10% FBS, 0.05% TWEEN® detergent 20, and plates incubated 2–4 hours at room temperature. Thereafter, plates were washed 4 times with PBS-TWEEN® detergent, and the respective detection antibodies for the cytokines were added at 1 μg/ml in PBS-TWEEN® detergent containing 10% FCS. Plates were incubated at RT 1 hour and washed 4 times in PBS-Tween before streptavidin-peroxidase conjugate (Boehringer, Indianapolis, Ind.) was added at 1:1000 dilution. After a 30-min. incubation at room temperature the color-substrate solution (ABTS) was added and left on the plates for 10–30 minutes. Plates were then counted in an ELISA reader at 490 nm. The results are shown in Table 1 immediately below.

TABLE 1

| Source of transferred cells | Prior to transfer, in vitro stimulated with: | Cytokines produced after 3 days of in vitro stimulation (ng/100 μl) | | Outcome (% IDDM in recipient mice) |
|---|---|---|---|---|
| | | IL-4 | IFN$_\gamma$ | |
| No cells | N/A | /A | N/A | 100 |
| $5 \times 10^6$ splenocytes from pCMV-Ins-B protected mouse | Porcine B chain | 0.21 +/− 0.09 | 0.12 +/− 0.01 | 50 |
| | Porcine B-chain, CD8 depleted | 0.3 +/− 0.12 | 0.2 +/− 0.15 | 0 |
| | LCMV | <0.05 | 1.1 +/− 0.1 | 100 |
| $5 \times 10^6$ splenocytes from pCMV-NP non-protected mouse | Porcine B chain | <0.05 | 0.19 +/− 0.08 | 83 |
| | LCMV | <0.05 | 1.5 +/− 0.4 | 100 |

After 8 days of culture, $5 \times 10^6$ cells were transferred into RIP-NP recipient mice (six mice per group), which had been infected with LCMV 5 days prior to transfer. The cells were transferred as follows:

Splenocytes were harvested from protected (pCMV-ins-B treated) or not-protected (PCMV-NP treated) mice 28 to 45 days after infection with LCMV and cultivated in 24-well tissue culture plates in 7% RPMI containing antibiotics and glutamine. As indicated, irradiated LCMV-infected macrophages from syngeneic H-$2^d$ (Balb/c) mice or syngeneic splenocytes coated with insulin B-chain or LCMV NP peptide (RPQASGVYM) at 1 mg/ml (SEQ ID NO:1) or infected with LCMV were used as antigen presenting cells. Cytokines were assayed in tissue culture supernatants 3 days and one week after culture and cells were adoptively transferred in to syngeneic RIP-NP transgenic recipients after 8 days intraperitoneally. Prior to transfer, all cells were washed 3 times in PBS.

As shown in Table 1, blood glucose levels in the recipient mice were analyzed for 2 to 3 months to determine the incidence of IDDM. CD8 depletion was carried out in vitro by using magnetic beads coupled to $\alpha$-CD8 and a subtraction column as suggested by the manufacturer (Dynal, Lake Success, N.Y.).

EXAMPLE IV

Reduction of Self-Reactive (LCMV-NP) CTL Activity in pCMV-B Protected Mice

Spleens and pancreatic draining lymph nodes were harvested from protected, pCMV-B vaccinated (protocol #1 of FIG. 1) RIP-NP mice and diabetic untreated RIP-NP mice. ELISPOT®-assays for IFN-$\gamma$ production in the presence of LCMV-$NP_{118-126}$ MHC class I peptide (36 hours) were performed as described immediately below. Two mice per group were tested in two different experiments. Protected and control mice were euthanized 4 months post LCMV, diabetic mice 3 weeks post LCMV.

ELISPOT® assays for $\gamma$-IFN production were performed as described in which is incorporated herein by reference. In addition, to assure an LCMV-NP antigen specific signal, each spleen or lymph node sample was incubated directly during the ELISPOT® assay with or without LCMV-$NP_{118-126}$ H-$2^d$ peptide for 36 hours at 37° C. in 5% $CO_2$. Background spots appearing in non-peptide stimulated cultures (0–3 spots/well) were subtracted from those found in peptide treated cultures (0–100 spots=readout range). Serial five-fold dilutions were done for each sample ranging from $2\times10^5$ to $10^3$. The results are shown in Table 2 immediately below.

TABLE 2

|  |  | IFN-$\gamma^+$ pCTL Spleen | IFN-$\gamma^+$ pCTL Pancreatic Draining Lymph Node |
|---|---|---|---|
| Control NP$^-$ |  | 1/2,777 | 1/3,250 |
| Protected NP$^+$ | Mouse 1 | 1/1,850 | 1/200,000 |
| PCMV-B | Mouse 2 | 1/4,230 | 1/35,000 |
| Diabetic NP$^+$ | Mouse 1 | 1/3,150 | 1/1,800 |
|  | Mouse 2 | 1/2,200 | 1/2,560 |

Table 2 clearly shows a local reduction of self-reactive (LCMV-NP) CTL activity in pancreatic draining lymph nodes of pCMV-B protected mice

EXAMPLE V

Effects of Vaccination on LCMV-specific CTL Levels

LCMV specific primary CTL activities and precursor CTL (pCTL) were assessed in groups of 2 to 3 RIP-NP transgenic mice 7 days post infection with LCMV and after administration of pCMV-ins-B or pCMV-NP plasmids or peptides/proteins orally (days 0, 7, 14 and 21 post infection) as described in Example 1. For precursor CTL the mean is shown, standard error was not more than 20%. Incidence of IDDM was determined as described in the procedure section in RIP-NP mice treated with pCMV-ins-B (protocol 1 of FIG. 1) or pCMV-NP (protocol 1, 2 or 3 of FIG. 1). Oral administration of insulin B-chain or LCMV H-$2^d$ NP peptides was achieved via gavage (500 $\mu$g twice weekly) as described in Example 1. CTL and pCTL levels were determined as set forth immediately below.

LCMV-specific CTL activity in spleens harvested 7 days after inoculation with $10^5$ LCMV ARM i.p. was assessed in a standard 4 to 5 hour $^{51}$Cr release assay on LCMV-infected and uninfected, MHC-matched [Balb/c17(H$2^d$)] and mismatched [MC57(H-$2^b$)] target cells. For determination of LCMV-specific CTL precursor (pCTL) frequency 7 days after infection, spleen cells from immunized mice were serial diluted and cultured in 96 well flat-bottom plates (12 wells per dilution, highest dilution: 16000 cells per well) with LCMV infected and irradiated (2000 rads) macrophages as well as irradiated spleen cells. After 8 days, cells from each well were split and tested on LCMV infected and uninfected Balb/c17 targets in a 4 to 5 hour $^{51}$Cr-release assay. pCTL frequencies were assessed by plotting the fraction of negative cultures on a semi-logarithmic scale against the number of splenocytes per culture. pCTL frequencies are defined by the slope of the linear regression among at least three separate data points. Positive cultures were defined by specific $Cr^{51}$ release >than 3 standard errors above background lysis. The results are shown in Table 3 immediately below and graphically represented in FIG. 3.

TABLE 3

| Immunizations of RIP-NP BALB/c mice | CMV-specific CTL | | Incidence of IDDM (%) |
|---|---|---|---|
|  | CTL (% $Cr^{51}$) | pCTL |  |
| None InsB | 60 ± 12 | 1 in 280 | 100 |
| Protein, p.o. | 62 ± 11 | 1 in 310 | 40 |
| DNA, i.m. | 58 ± 9 | 1 in 180 | 55 |
| LCMV NP |  |  |  |
| Peptide, p.o. | 20 ± 8 | 1 in 980 | 100 |
| DNA, i.m. | 22 ± 4 | 1 in 750 | 100 |

Figure 3:
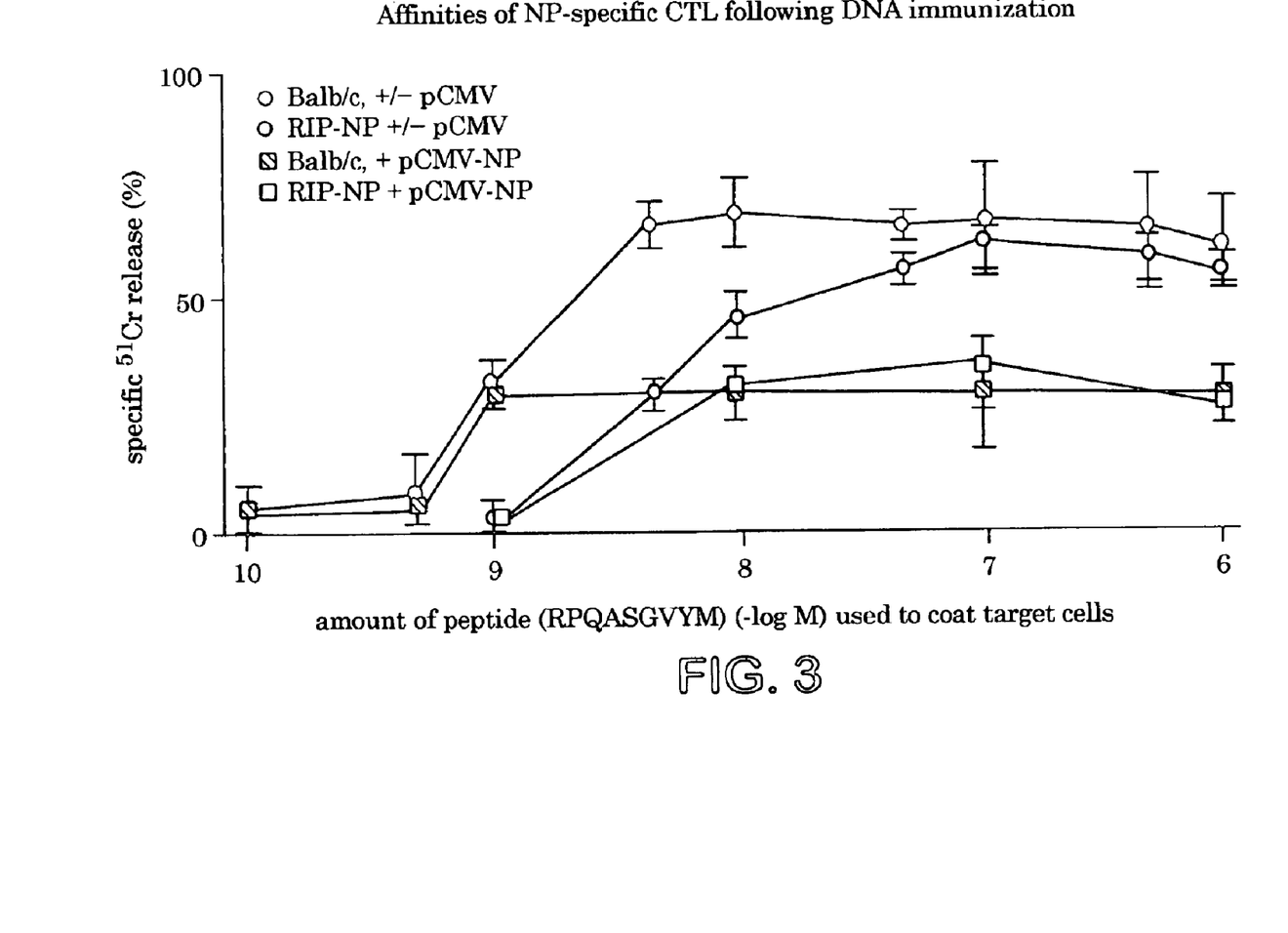
FIG. 3 shows affinities of LCMV-NP CTL using serial log dilutions of LCMV-NP H-2d peptide (SEQ ID NO:1) on syngeneic Balb/c targets in a 5 hour 51 Cr release assay. Three mice per group were injected with PCMV or PCMV-NP according to protocol 2, of FIG. 1. The overall plateau release was decreased in PCMV-NP treated groups compared to PCMV treated controls, however, the fall-off of the curve was not shifted, indicating that there were no significant affinity differences.

Both Table 3 and FIG. 3 clearly show that LCMV-specific CTLs are reduced following administration of LCMV-NP, but not after administration ins-B.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited to the particular embodiments which have been described in detail herein. Rather, reference should be made to the appended claims as indicative of the scope and content of the invention.

I claim:

1. An immunomodulating composition for treating autoimmune diabetes, said composition comprising one or more nucleic acid constructs encoding GAD self-antigen and IL-10 in a pharmaceutically acceptable carrier.

2. The composition of claim 1, wherein the autoimmune diabetes is type I diabetes.

3. The composition of claim 1, wherein the nucleic acid constructs further comprise a regulatory element operatively linked to the nucleic acid encoding the self-antigen or the IL-10.

4. The composition of claim 3, wherein the regulatory element is a promoter selected from the group consisting of Mouse Mammary Tumor Virus (MMTV) promoter, Human Immunodeficiency Virus Long Terminal Repeat (HIV LTR) promoter, Moloney virus promoter, ALV promoter, Cytomegalovirus (CMV) promoter, human Actin promoter, human Myosin promoter, RSV promoter, human Hemoglobin promoter, human muscle creatine promoter and EBV promoter.

5. An immunomodulating composition for treating autoimmune diabetes, said composition comprising one or more nucleic acid constructs encoding an insulin B-chain self-antigen and a cytokine selected from the group consisting of IL-10, IL-4, and a combination thereof, in a pharmaceutically acceptable carrier.

6. The composition of claim 5, wherein the autoimmune diabetes is type I diabetes.

7. The composition of claim 5, wherein the nucleic acid constructs further comprise a regulatory element operatively linked to the nucleic acid encoding the self-antigen or the cytokine.

8. The composition of claim 7, wherein the regulatory element is a promoter selected from the group consisting of Mouse Mammary Tumor Virus (MMTV) promoter, Human Immunodeficiency Virus Long Terminal Repeat (HIV LTR) promoter, Moloney virus promoter, ALV promoter, Cytomegalovirus (CMV) promoter, human Actin promoter, human Myosin promoter, RSV promoter, human Hemoglobin promoter, human muscle creatine promoter and EBV promoter.

\* \* \* \* \*